(12) United States Patent
Chaudhry

(10) Patent No.: US 10,335,421 B1
(45) Date of Patent: Jul. 2, 2019

(54) TOPICAL WOUND CARE FORMULATION

(71) Applicant: Aisha Chaudhry, Bensalem, PA (US)

(72) Inventor: Aisha Chaudhry, Bensalem, PA (US)

( * ) Notice: Subject to any disclaimer, the term of this patent is extended or adjusted under 35 U.S.C. 154(b) by 0 days.

(21) Appl. No.: 15/905,632

(22) Filed: Feb. 26, 2018

(51) Int. Cl.
  *A61K 9/00* (2006.01)
  *A61K 36/61* (2006.01)
  *A61K 38/18* (2006.01)
  *A61K 31/045* (2006.01)
  *A61K 31/125* (2006.01)
  *A61K 31/635* (2006.01)

(52) U.S. Cl.
  CPC .......... *A61K 31/635* (2013.01); *A61K 9/0014* (2013.01); *A61K 31/045* (2013.01); *A61K 31/125* (2013.01); *A61K 36/61* (2013.01); *A61K 38/1808* (2013.01)

(58) Field of Classification Search
  None
  See application file for complete search history.

(56) References Cited

FOREIGN PATENT DOCUMENTS

| CN | 1275616 C | * | 9/2006 |
| CN | 101647851 A | * | 2/2010 |

OTHER PUBLICATIONS

CN1275616C (translation, Google Patents) (Year: 2006).*
CN101647851A (translation, Google Patents) (Year: 2010).*
Amazon (Canada) Hebermin product page, https://www.amazon.ca/Hebernnin-Facdermin-Cream-Burn-Treatnnent/dp/B01FZAJUWS; ASIN: B01FZAJUWS (Year: 2016).*

* cited by examiner

*Primary Examiner* — Michael Barker
(74) *Attorney, Agent, or Firm* — Zeman-Mullen & Ford, LLP

(57) ABSTRACT

The disclosed wound-healing formulation adds ingredients from the group consisting of camphor, menthol and eucalyptus to known silver sulfadiazine-based formulations, or to known silver sulfadiazine-and-urogastrone-based formulations, preferably for the topical treatment of skin wounds such as cuts, burns, surgical wounds, etc. Preferred embodiments are in cream form. The disclosed formulation shows unexpected and startling improvement in wound healing rates over expected healing rates using the known silver sulfadiazine-based or silver sulfadiazine-and-urogastrone-based formulations alone.

4 Claims, No Drawings

TOPICAL WOUND CARE FORMULATION

RELATED APPLICATIONS

None.

FIELD OF THE DISCLOSURE

This disclosure is directed generally to a wound care formulation, preferably in cream form, that is both stable and bioeffective. Broadly, and without limiting the scope of this disclosure, one embodiment of the formulation is a urogastrone camphor eucalyptus menthol cream formulation for topical administration in a silver sulfadiazine base containing propylene glycol. Additional embodiments are also disclosed.

BACKGROUND OF THE DISCLOSED TECHNOLOGY

Antimicrobial creams are known to promote skin and soft tissue wound healing via topical administration. Such antimicrobial creams typically demonstrate improvement in wound healing as well as more rapid closure of wounds. In this way, such topical antimicrobial creams decrease infection and inflammation commonly associated with wounds, scars, and burns. More specifically, topical antimicrobial creams will generally relieve redness and inflammation, and will increase the speed and quality of wound healing. There is a correlation between the therapeutic effects of these creams and their healing potentials.

Topical antimicrobial products are commercially available in various media, such as lotions, creams, ointments, and gels. A key active ingredient in one class of commercially-available antimicrobial creams is silver sulfadiazine. Hebermin and Silvadene® are brand names for known topical antimicrobial creams containing silver sulfadiazine. Each demonstrate serviceable healing performance in the treatment of skin wounds.

Hebermin is stated as having the following ingredients: Silver sulfadiazine 1%, urogastrone 0.001%, stearyl alcohol, petrolatum, polyoxyl 40 stearate, propylene glycol, isopropyl myristate, and sorbitan monooleate with methylparaben 0.3%.

Silvadene® is stated as having similar ingredients to Hebermin without the urogastrone.

It is always advantageous to reduce the healing time for skin wounds. The quicker a wound heals, the less downtime the patient sustains with limited mobility and discomfort. Quicker healing also reduces the risk of infection. It would therefore be highly advantageous if the healing performance of existing silver sulfadiazine-based topical creams such as Hebermin and Silvadene® could be accelerated to provide even better healing performance in a shorter period of time.

SUMMARY AND TECHNICAL ADVANTAGES

These and other drawbacks in the prior art are addressed by the disclosed embodiments of an inventive formulation that, in currently preferred embodiments, is administered to wounds in topical cream form. Although currently preferred embodiments of the formulation are in cream form, it will be nonetheless appreciated that the scope of this disclosure is not limited in this regard. Other embodiments of the disclosed formulation may be, for example, in solution form. The cream is currently branded "Compone CS". Disclosed embodiments of the inventive formulation add ingredients from the group consisting of camphor, menthol and eucalyptus to known silver sulfadiazine-based formulations such as Hebermin or Silvadene®. In embodiments where camphor is added, camphor is preferably added in quantities in a range between about 0.5% to about 20%, and more preferably in a range between about 10% to about 20%. In embodiments where menthol is added, menthol is preferably added in quantities in a range between about 1% to about 30%, and more preferably in a range between about 9% to about 30%. In embodiments in which eucalyptus is added, eucalyptus is preferably added in quantities in a range between about 2% to about 10%, and more preferably in a range between about 2% to about 5%. It will be nonetheless appreciated that the scope of the disclosed wound-healing formulation is not limited to the foregoing camphor, menthol and/or eucalyptus ingredient percentages.

Currently preferred embodiments of the disclosed wound-healing formulation are in cream form, are stable, and carry a biologically effective amount of silver sulfadiazine, urogastrone, and ingredients from the group consisting of camphor, menthol and eucalyptus. Such cream embodiments preferably also include balanced amounts of hydrophilic and lipophilic surfactants with other preservatives. The hydrophilic base creates and maintains the needed therapeutic concentration of the active ingredients in the precise area of the wound to be treated. Examples and actual cases show cream embodiments of the disclosed wound-healing formulation to be highly effective in stimulating cellular proliferation in wounds, while reducing bacterial growth. In particular, without limitation, the disclosed wound-healing formulation has shown itself to be highly effective against gram positive and gram negative bacteria, dermatophytes, and *candida* types of fungus.

One exemplary embodiment of the disclosed wound-healing formulation is according to the following formulation:

Silver sulfadiazine 1%
Urogastrone 0.001%
Water
Stearyl alcohol
Petrolatum
Polyoxyl 40 stearate
Isopropyl myristate
Sorbitan monooleate with methylparaben 0.3%
Propylene glycol
Camphor 5%
Menthol 10%
Eucalyptus 4%

It will be appreciated, however, that the foregoing embodiment is exemplary only, and that the scope of the disclosed wound-healing formulation is not limited to the foregoing embodiment.

Topically applied to wounds, embodiments of the disclosed wound-healing formulation substantially accelerate the healing rate over what might be expected in treatment with, for example, silver sulfadiazine/urogastrone (e.g. Hebermin) or silver sulfadiazine (e.g. Silvadene®) by itself. In more detail, the addition of ingredients from the group consisting of camphor, menthol and eucalyptus to known silver sulfadiazine-based formulations such as Hebermin or Silvadene® shows a remarkable, unexpected and unprecedented improvement in the rate of healing in the treatment of wounds. Embodiments of the disclosed wound-healing formulation have proven to be highly effective in the treatment of wounds including, without limitation, arterial wounds, venous wounds, post-operative and other surgical wounds, burns, dehisced wounds and ulcerations. Exemplary applications further include treating wounds secondary to injury, trauma burns, diabetes, ulcer treatment, radiation, acne scars, stasis dermatitis, and peripheral vascular disease ("PVD"). Embodiments of the disclosed formulation have proven to substantially decrease wound healing time as compared to corresponding healing time for wounds treated with known silver sulfadiazine-based formulations alone (i.e. without the additional camphor, menthol and/or eucalyptus). Embodiments of the disclosed wound-healing formulation have further proven to completely resolve some wounds treated where prior application of known silver sulfadiazine-based formulations, or treatment with known formulations consisting mainly of camphor, menthol and/or eucalyptus by themselves, proved not to be efficacious.

Topical administration of camphor, menthol and/or eucalyptus by themselves are well known for certain limited therapeutic effects. Camphor, menthol and eucalyptus are readily absorbed through the skin. The known therapeutic effects include soothing. Topically-applied camphor is known to selectively stimulate nerve endings sensitive to cold, producing a warm sensation when vigorously applied, or a cool sensation when applied gently. This known nerve stimulation effect also induces a slight local anesthesia, promotes blood flow to the contact region (vasodilation), and has an antimicrobial secondary effect. The sensation of heat or cold that camphor produces on the skin is known to be caused by activating an ion channel, which may in turn account for the antimicrobial secondary effect.

Topical administration of menthol by itself is also well known for certain therapeutic effects. For example, menthol is widely used in dentistry and oral care as a topical analgesic and antibacterial agent. Menthol's topical analgesic properties are also known in the relief of sprains, minor aches and pains. Well-known products such as "Bengay" or "Icy Hot" are known to contain menthol by itself or camphor with/menthol. Similar to camphor, topically-applied menthol also has a soothing effect arising from a cooling sensation felt in the areas on which it is administered. As such, menthol-based creams are known for the treatment of sunburn, for example.

Topical administration of eucalyptus by itself is also well known for relief of many of the same symptoms addressed by camphor and menthol. For example, topical administration of eucalyptus by itself is known for soothing, analgesic and antiseptic effects, as well as relief of itching (such as in pruritus). Eucalyptus is also known to lower blood sugar.

While topically-administered camphor, menthol and eucalyptus products are known to have the foregoing limited therapeutic effects by themselves, they are generally understood to provide "relief" rather than "healing". Many topical camphor, menthol and eucalyptus products are "over the counter" products, and are intended to provide relief of symptoms while the body engages its own natural healing process. Very little, if anything, in the known topical administration of camphor, menthol and eucalyptus products actually reduces healing time. Rather, as noted, the topical administration of camphor, menthol and eucalyptus products provides relief from discomfort while the body heals at its usual rate.

In sharp contrast, examples and actual case studies set forth in the "Detailed Description" section below demonstrate the unexpected and unprecedented improvement in the rate of healing in the treatment of skin wounds seen from the topical administration of embodiments of the disclosed wound-healing formulation (in which ingredients from the group consisting of camphor, menthol and eucalyptus are added to known silver sulfadiazine-based formulations).

Conventionally, the addition of such ingredients to known silver sulfadiazine-based formulations might have been expected to provide some relief of the patient's symptoms while the healing rate continued consistent with known healing rates seen in the administration of such known silver sulfadiazine-based formulations. Nothing (as of yet) cogently explains the unexpected and startling improvement in healing rate seen in the examples and case studies set forth below when ingredients from the group consisting of camphor, menthol and eucalyptus are added to the silver sulfadiazine-based formulations.

The unexpected improvement in wound healing rate seen with the disclosed wound-healing formulation manifests itself in unexpected rates of both epithelial and epidermal cell regeneration, and in the formation of new granulation tissue. Corresponding unexpected improvements are seen in the rate of protein production, collagen collection, and the formation of blood vessels during the healing process. In hindsight, none of these improved wound-healing rates or effects would be expected from the addition of ingredients such as camphor, menthol and/or eucalyptus to silver sulfadiazine-based formulations. However, further work is needed in this area to understand better, at the molecular or nano level, why ingredients from the group consisting of camphor, menthol and eucalyptus unexpectedly accelerate the rate of healing far beyond what might be expected if one or more of such ingredients had been added merely to provide known relief of symptoms.

It is therefore a technical advantage of the disclosed wound-healing formulation to accelerate the rate of healing of skin wounds such as cuts, burns, surgical wounds, etc.

Another technical advantage of the disclosed wound-healing formulation is to heal skin wounds whose healing has been unresponsive to treatment with conventional silver sulfadiazine-based formulations.

Another technical advantage of the disclosed wound-healing formulation lies in the delivery system of currently preferred embodiments in cream form. Delivery systems of topical drug products play an important role in the success and solidity of the product. The cream embodiments of the disclosed wound-healing formulation allow easy application of the product on the skin, and good absorption of the active ingredients into the wound being treated.

A further technical advantage of the disclosed wound-healing formulation is that embodiments thereof in cream form are stable. Long term stability is important in the commercialization of a cream commodity, in order to sustain a commercially viable shelf life.

A further technical advantage of the disclosed wound-healing formulation is that wounds healed with the formulation generally have a pleasing cosmetic appearance.

According to a first aspect, therefore, this disclosure describes embodiments of a topical formulation, comprising: (a) silver sulfadiazine; and (b) at least one ingredient selected from the group consisting of: (1) camphor; (2) menthol; and (3) eucalyptus. In some embodiments, the formulation may further comprise (c) urogastrone. In some embodiments, the formulation may further comprise at least two ingredients selected from the group consisting of: (1) camphor; (2) menthol; and (3) eucalyptus, which embodiments may further comprise (c) urogastrone. In some embodiments, the formulation may include about 1% silver sulfadiazine. In some embodiments, the formulation may include about 0.001% urogastrone. In some embodiments, the formulation may include about 0.5% to about 20% camphor. In some embodiments, the formulation may include about 1% to about 30% menthol. In some embodiments, the formulation may include about 2% to about 10% eucalyptus. In some embodiments, the formulation may include about 0.5% to about 20% camphor and about 1% to about 30% menthol. In some embodiments, the formulation may include about 0.5% to about 20% camphor and about 2% to about 10% eucalyptus. In some embodiments, the formulation may include about 1% to about 30% menthol and about 2% to about 10% eucalyptus.

According to a second aspect, this disclosure describes embodiments of a topical formulation, comprising: (a) silver sulfadiazine; (b) camphor; (c) menthol; and (d) eucalyptus. In some embodiments, the formulation may further comprise (e) urogastrone. In some embodiments, the formulation may include about 1% silver sulfadiazine. In some embodiments, the formulation may include about 0.001% urogastrone. In some embodiments, the formulation may include about 0.5% to about 20% camphor, about 1% to about 30% menthol, and about 2% to about 10% eucalyptus.

According to a third aspect, this disclosure describes embodiments of a topical formulation, comprising: (a) about 1% silver sulfadiazine; (b) about 0.001% urogastrone; and (c) at least one ingredient selected from the group consisting of: (1) about 0.5% to about 20%/0 camphor; (2) about 1% to about 30% menthol; and (3) about 2% to about 10% eucalyptus. In other embodiments, the formulation may further comprise at least two ingredients selected from the group consisting of: (1) about 0.5% to about 20% camphor; (2) about 1% to about 30% menthol; and (3) about 2% to about 10% eucalyptus.

The foregoing has outlined rather broadly some of the features and technical advantages of the disclosed wound-healing formulation, in order that the detailed description that follows may be better understood. Additional features and advantages of the disclosed wound-healing formulation may be described. It should be appreciated by those skilled in the art that the conception and the specific embodiments disclosed may be readily utilized as a basis for modifying or designing other formulations for carrying out the same inventive purposes of the disclosed technology, and that these equivalent formulations do not depart from the spirit and scope of the technology as described and as set forth in the appended claims.

DETAILED DESCRIPTION

As noted above in the "Summary" section, the disclosed wound-healing formulation, currently branded "Compone CS", is an effective drug with excellent anti-microbial, wound healing, bactericidal properties. In test cases, topical administration of embodiments of the disclosed wound-healing formulation in cream form have demonstrated substantially increased epithelization, substantially increased production of granulation, and substantially increased cellular proliferation. The cream has demonstrated significant reduction in the amount of time required to achieve an area of granulation necessary to close wounds. The cream is further useful in wound treatment by extravasation of cytostatics. As a result, the time for wounds to heal and become closed has substantially decreased as compared to known silver sulfadiazine-based compounds.

The following are examples and actual cases demonstrating the remarkably increased healing rate of wounds treated with cream embodiments of the disclosed wound-healing formulation.

Example 1

Patient presented with a post-operative left plantar heel wound following a deep surgical excision to remove an invasive carcinoma. Artificial skin grafts were applied, but were unsuccessful. Topical application of conventional silver-sulfadiazine-based and other wound care creams also failed completely. Such unsuccessful conventional products included Silvadene, Santyl, Medi-Honey, Betadine, and Dakin's Solution. A cream embodiment of the disclosed wound-healing formulation was prepared comprising the following ingredients: silver sulfadiazine 1%, urogastrone 0.001%, water, stearyl alcohol, petrolatum, polyoxyl 40 stearate, propylene glycol, isopropyl myristate, sorbitan monooleate with 0.3% methylparaben, camphor 5%, menthol 10% and eucalyptus 4%. The temperature was adjusted between 65-75 degrees F. (+/−) 5 degrees F., and was prepared by stirring continuously for 5 to 10 minutes. The resulting mixture was thoroughly kneaded into a smooth cream which appeared uniform in composition. The cream was applied every 48 hours to patient's left plantar heel wound. Wound was cleansed with normal saline solution, followed by topical application of cream directly onto the wound and covered by a dry, sterile dressing. The wound healed completely in approximately 6 weeks. Patient was monitored throughout the study for any adverse reaction or experience. None were reported.

Example 2

Patient was a 38-year old diabetic male with a rare skin disorder. The rare skin disorder consisted of 1" thick callus/hypertrophic skin which covered the entire plantar aspect of bilateral feet, extending from the metatarsal heads to both heels. Many different physicians had previously attempted treatment with multiple conventional topical wound care agents including Santyl, Accuzyme, Panafil, Betadine, Dakin's Solution, Eucerin cream, silver sulfadiazine-based formulations, menthol topical solutions (by themselves), and anti-bacterial topical creams. After several months of no improvement with such conventional wound care agents, patient underwent surgery followed by topical wound care. The callus tissue was resected in the operating room. This created various ulcerations noted on the entire plantar aspect of each foot (respectively, Wagner stage 2 to stage 3 ulcerations). Patient was given different creams for treatment, including Medihoney, Emuaid, polysporin, Santyl, Silvadene, Betadine, Collagen dressings, and Mepitel films. All of these were unsuccessful after several months of use. Then, a cream embodiment of the disclosed wound-healing formulation was prepared comprising the following ingredients: silver sulfadiazine 1%, urogastrone 0.001%, water, stearyl alcohol, petrolatum, polyoxyl 40 stearate, propylene glycol, isopropyl myristate, sorbitan monooleate with 0.3% methylparaben, camphor 5%, menthol 10% and eucalyptus 4%. This preparation was then applied to the left plantar wound. The wound healed completely, and so the same treatment was applied to the right plantar wound. Both wounds healed successfully within four weeks. Patient has been seen for approximately one year post-operatively with no recurrence of wounds, and no further breakdown has been noted.

Example 3

Patient was a 57-year old non-insulin dependent diabetic female with venous insufficiency of bilateral legs and feet. Her medical history included hypertension, NIDDM, high cholesterol, diabetic neuropathy, and depression. Patient also had a history of a stroke. The patient had 3 wounds located on the left distal third of the anterior leg. Wounds were approximately 1-2 cm apart from one another. The most proximal wound measured 2 cm×2 cm×1 cm; the wound was fibro-granular in nature with significant serous drainage noted from the wounds. The second, middle wound was 1.5 cm×1.5 cm×1 cm, and was also fibro-granular in nature. The third, most distal wound was 2 cm×1 cm×0.5 cm and fibro-granular in nature. Wounds were approximately 50% fibrotic and 50% granular. Patient had been previously treated unsuccessfully with multiple topical agents including conventional silver-sulfadiazine formulations. Such prior treatments inchluded weekly debridements, topical debriding agents, absorbing agents, and oral antibiotics as well as multi-vitamins. Patient was seen twice a week for four weeks. Initially, the wounds were sharply debrided and all fibrotic tissue was removed. Then, a cream embodiment of the disclosed wound-healing formulation was prepared comprising the following ingredients: silver sulfadiazine 1%, urogastrone 0.001%, water, stearyl alcohol, petrolatum, polyoxyl 40 stearate, propylene glycol, isopropyl myristate, sorbitan monooleate with 0.3% methylparaben, camphor 5%, menthol 10% and eucalyptus 4%. This cream was applied to a healthy, granular wound base twice a week for four weeks. Wound was dressed with 4×4s, kling, and a kerlix dressing. The cream was uniformly applied throughout the entire aspect of all three wound beds. A significant decrease in wound size and change in composition of wound bed was evident in weeks 1 and 2. There was almost complete resolution by week 3. The wounds had completely resolved and healed after 4 weeks. The skin was adequately covering what had previously been exposed wound beds. Dressings were no longer needed at this time and the patient is now seen for a routine follow up every 3-6 months. Patient has been stable with no recurrence of wounds.

Example 4

Patient was a 49-year old insulin dependent diabetic male with hypertension and hypothyroidism and significant past medical history. Patient underwent left foot cheilectomy. The wound began dehiscing 7 days post-operatively. Sutures loosened and a 2 inch linear incision site wound occurred. The wound was noted to 2 cm×0.25 cm×0.1 cm in dimension. It was fibro-granular in nature and approximately 80% was fibrotic and 20% granular with serous drainage noted. Patient was given post-operative antibiotic throughout the post-operative care time frame. Many conventional wound care topical products were initially used in attempts to heal surgical wound, including silver sulfadiazine-based formulations, Santyl, collagen dressings, hydrocolloid dressings, and alginates. After 4 weeks, there was no improvement in wound healing with sharp debridement and topical wound care products. Accordingly, a cream embodiment of the disclosed wound-healing formulation was prepared comprising the following ingredients: silver sulfadiazine 1%, urogastrone 0.001%, water, stearyl alcohol, petrolatum, polyoxyl 40 stearate, propylene glycol, isopropyl myristate, sorbitan monooleate with 0.3% methylparaben, camphor 5%, menthol 10% and eucalyptus 4%. This preparation was then applied every 3 days to the wound bed and covered with 4×4s, kling and kerlix dressings. Wound measurements were taken every 3 days at every dressing change and improvement was noted in both dimension and appearance of wound bed. After 4 weeks of continuous treatment after every 3 days, the wound was completely closed with no dehiscence remaining. The patient had no recurrence of the wound.

Example 5

Patient was a 33-year old male with a non-healing left hallux wound. Patient had no significant past medical history, no known drug allergies and prior surgeries consistent with tonsillectomy, hemorrhoid resection, and hernia repair. Patient had left hallux nail removed. Left hallux dorsal wound remained post-procedurally. The wound measured 1.5 cm×1.5 cm×0.1 cm. The wound had slight serous drainage noted. Initial wound treatment comprised of 4 weeks of application of betadine and topical bacitracin ointment with no improvement. Following this treatment, camphor cream was applied by itself twice daily to left hallux wound site. Minimal improvement was noted after 30 days of treatment. Upon day 30, the wound measurement was noted to be 1.5 cm×125 cm×0.2 cm on the dorsal aspect of the left hallux. Mild serous drainage was noted, as was noted initially. At this time, camphor topical cream treatment was discontinued and topical menthol-eucalyptus cream mixture was applied to left hallux dorsal wound, twice daily for 30 days. Serial, weekly debridements of the left hallux wound bed were performed with a #15 surgical blade and a sharp curette. After 30 days of treatment, wound measurements were taken and the wound size was measured to be approximately 1.25 cm×1.25 cm×0.1 cm. Very mild improvement was noted. Menthol-eucalyptus cream treatment was halted. A cream embodiment of the disclosed wound-healing formulation was prepared comprising the following ingredients: silver sulfadiazine 1%, urogastrone 0.001%, water, stearyl alcohol, petrolatum, polyoxyl 40 stearate, propylene glycol, isopropyl myristate, sorbitan monooleate with 0.3% methylparaben, camphor 5%, menthol 10% and eucalyptus 4%. This preparation was then applied to the wound bed. As noted, upon initial application, the left dorsal hallux wound measured 1.25 cm×1.25 cm×0.1 cm. Slight serous drainage was also noted. The wound was noted to be fibrogranular in nature. The disclosed wound-healing formulation was applied once daily to the left hallux. Debridement of the wound continued to occur once a week and serial measurements were taken. After one week's treatment with the disclosed wound-healing formulation, the wound was measured to be 1 cm×1 cm×0.1 cm. Treatment continued with a similar regimen in week 2. After 14 days, wound measurements were again taken. The wound was measured to be 0.9 cm×0.7 cm×0.1 cm. Mild serous drainage was again noted. With improvement noted, it was decided that the same regimen would continue. Treatment continued with a similar regimen in week 3. At the end of the 3$^{rd}$ week, measurements were again taken. The wound was measured and noted to be 0.5 cm×0.5 cm×0.1 cm in depth. The regimen was continued for week 4, during which the wound was again debrided and the disclosed wound-healing formulation was applied daily. At day 32, the wound had completely resolved. The wound has not returned after 1 year of follow up and no further treatment.

Example 6

Patient was a 78-year old female with a past medical history of NIDDM and atrial fibrillation. Her past surgical history was significant for multiple foot surgeries including amputations of two digits on the left foot and amputation of a digit on the right foot. Also significant for past surgical history was cataract surgery, OU, gallbladder surgery, and carpal tunnel release to bilateral hands. Patient presented with a plantar hallux, non-healing wound, which measured 1 cm×1 cm×0.5 cm in depth. The wound was noted to have serosanguinous drainage for several months. During this time, the wound was cleansed daily with saline and a conventional silver-sulfadiazine urogastrone cream (Hebermin) was applied as a first line of treatment. The wound was debrided once a week with a #15 surgical blade and a curette to remove all fibrotic, nonviable tissue from the wound bed. The wound bed was then dressed with betadine, adaptic, 4×4s, and a light kling dressing. Hebermin was used consistently for 3 months. Weekly measurements of the wound were taken. Wound measurements went from 1 cm×1 cm×0.5 cm initially, to 0.8 cm×0.7 cm×0.5 cm after three months of Hebermin treatment. Patient's wound showed minimal improvement during the initial 3-month Hebermin treatment, during which time patent also faced multiple episodes of cellulitis (which was treated with multiple antibiotics, including Clindamycin, Zithromax, and Bactrim DS). Hebermin cream alone was not adequate for wound healing. Patient's wound was then treated for 3 months with a combination of camphor-eucalyptus-menthol cream, which was again applied daily to the wound on the left plantar hallux. Wound measurements started at 0.8 cm×0.7 cm×0.5 cm. Mild serous drainage was noted. Weekly debridements continued and weekly measurements were taken. Wound measurements decreased to 0.7 cm×0.6 cm×0.4 cm after 3 months of camphor-eucalyptus-menthol cream treatment. Stagnation of wound healing solidified reasoning for a need for new treatment. At month 6, treatment was changed to the disclosed wound-healing formulation. A cream embodiment of the disclosed wound-healing formulation was prepared comprising the following ingredients: silver sulfadiazine 1%, urogastrone 0.001%, water, stearyl alcohol, petrolatum, polyoxyl 40 stearate, propylene glycol, isopropyl myristate, sorbitan monooleate with 0.3% methylparaben, camphor 5%, menthol 10% and eucalyptus 4%. This preparation was applied once daily to the plantar left hallux. As noted, initial wound measurements were 0.7 cm×0.6 cm×0.4 cm. ABI testing was performed and adequate perfusion was noted. After daily applications of the disclosed wound-healing formulation and weekly debridements with the use of a #15 surgical blade and curette as previously performed, the wound dimensions decreased significantly. After 3 weeks of continued use, the wound completely resolved. No drainage, nor infection persisted. After 9 months post-wound healing of the left hallux plantar wound, the patient continued to be wound free and ambulate with no difficulty.

The disclosed wound-healing formulation has been described above with reference to specific examples and actual cases in which embodiments thereof were administered to promote healing of skin wounds such, as for, example, arterial wounds, venous wounds, post-operative and other surgical wounds, burns, dehisced wounds and ulcerations. It will be appreciated that the disclosed wound-healing formulation is not limited to these exemplary cases and these applications.

Although the inventive material in this disclosure has been described in detail along with some of its technical advantages, it will be understood that various changes, substitutions and alternations may be made to the detailed embodiments without departing from the broader spirit and scope of such inventive material as set forth in the following claims.

We claim:

1. A topical formulation, comprising:
   (a) silver sulfadiazine;
   (b) urogastrone;
   (c) camphor;
   (d) menthol; and
   (e) eucalyptus.

2. The formulation of claim 1, in which the formulation includes about 0.5% to about 20% camphor, about 1% to about 30% menthol, and about 2% to about 10% eucalyptus.

3. The formulation of claim 2, in which the formulation includes about 1% silver sulfadiazine.

4. The formulation of claim 2, in which the formulation includes about 0.001% urogastrone.

* * * * *